United States Patent [19]

Hunter et al.

[11] Patent Number: 4,642,395

[45] Date of Patent: Feb. 10, 1987

[54] POISONING OF RESIN SUPPORTED CATALYST

[75] Inventors: Douglas L. Hunter; Stanley E. Moore, both of Lake Jackson, Tex.

[73] Assignee: The Dow Chemical Company, Midland, Mich.

[21] Appl. No.: 799,237

[22] Filed: Nov. 18, 1985

[51] Int. Cl.$^4$ .............................................. C07C 29/16
[52] U.S. Cl. .................................... 568/883; 568/451
[58] Field of Search ............... 568/909, 451, 884, 454, 568/909, 882, 883, 451

[56] References Cited

U.S. PATENT DOCUMENTS 4,197,414  4/1980  Hartwell .............................. 568/909
4,306,085  12/1981  Kim et al. ............................ 568/909

*Primary Examiner*—Werren B. Lone
*Attorney, Agent, or Firm*—B. G. Colley

[57] ABSTRACT

A combined hydroformylation/reduction reaction is enhanced by the control of halide concentration in the feed olefin, solvent and solid supported transition metal complex catalyst to produce higher initial reaction rate and longer catalyst life.

16 Claims, No Drawings

POISONING OF RESIN SUPPORTED CATALYST

FIELD OF THE INVENTION

This invention relates to the production of aldehydes and alcohols by the hydroformylation/reduction reaction of olefins with hydrogen and carbon monoxide in the presence of a transition metal complex catalyst supported by a polymer or resin.

BACKGROUND OF THE DISCLOSURE

The reaction of an olefin with hydrogen and carbon monoxide to produce alcohols is the well known hydroformylation/reduction reaction also known as the oxo reaction. One art-recognized oxo method of preparing alcohols from olefins is a two-step process wherein the first step is contacting at elevated temperature and pressure an olefin with a synthesis gas mixture of hydrogen and carbon monoxide in the presence of an oxo catalyst to produce a mixture of aldehydes; then, in the second step, these aldehydes are hydrogenated to their corresponding alcohols. A one-step oxo process for the production of alcohols utilizes a cobalt carbonyl phosphine catalyst. Cobalt and rhodium are frequently used as the oxo catalysts. The classical oxo catalyst precursor is octocarbonyldicobalt, $Co_2(CO)_8$, formed by reaction of metallic cobalt with carbon monoxide. The complex $RhH(CO)(Ph_3P)_3$ is even more efficient than the cobalt complex at promoting the oxo reaction.

The oxo process was discovered in Germany during World War II, and was the first industrial application of catalysis by a transition metal complex. When using homogeneous catalysis with transition metal complex catalysts that are soluble in the liquid reaction mixture during the hydroformylation/reduction reaction, there is a recovery and regeneration step necessary for cost reduction for the dissolved transition metal catalyst due to the expense of the metal itself and the need to minimize loss. Even with sophisticated recovery methods, small losses of metal will occur, thus the economic use of homogeneous catalysis using a transition metal complex catalyst is limited.

Heterogeneous catalysis can be done in the oxo reaction using a catalyst containing a transition metal complex supported upon solid polymers or resins. However, the problem with metal leaching from the solid-supported catalyst is still a major consideration due to the high cost of recovery or replacement of the transition metal catalyst. This metal leaching occurs because some species in the oxo process is a better ligand, forming a stronger bond with the metal complex than the ligand functionality of the solid support. Garrou et al, U.S. Pat. No. 4,262,147 and Hartwell et al, U.S. Pat. No. 4,144,191 discuss catalysts of transition metal complexes supported by amine resins. Haag et al, U.S. Pat. No. 4,098,727 teaches use of a polymer as a solid support for transition metal complexes which then are less soluble in the liquid reaction mixture due to strong chemical bonds between the polymer and the metal complex. In the Haag et al patent, polystyrene resins with tertiary amine functional groups serve as a solid support for a rhodium catalyst prepared using $RhCl_3 \cdot XH_2O$.

The inventive concept of this disclosure is the unexpected recognition that halogens, specifically chlorine, poison or inhibit the hydroformylation/reduction reaction of olefins to alcohols using a rhodium catalyst on a tertiary amine resin. As a result of this invention, a combined hydroformylation/reduction reaction is enhanced because catalyst reactivity is greater and catalyst life is longer. That halogens are a poison was not expected since U.S. Pat. No. 4,098,727 teaches using $RhCl_3XH_2O$ to prepare a rhodium catalyst containing 2.23% chlorine.

DETAILED DESCRIPTION OF THE INVENTION

The prior art teaches the use of polystyrene resins with tertiary amine functional groups to serve as catalyst support for rhodium to hydroformylate and reduce olefins to alcohols. In the process, the catalyst actually comes off the resin and thus acts as a homogeneous catalyst but returns to the resin as the alcohol product concentration increases. The metal portion of the catalyst is chemically bonded to the polymer portion prior to use in the process; thus, the catalyst is only soluble to the extent that the metal is temporarily soluble. Since the polymer is insoluble in the reactants and reaction products, the metal portion of the catalyst remains insoluble while it is bonded to the polymer. Under certain conditions the essentially insoluble catalyst can be used in liquid phase operations for long periods of time. Stated otherwise, the metal portion of the catalyst can be controlled to sustain an insoluble state, giving the benefit of the insoluble resin for the entire catalyst. The use of this catalyst system allows simplified processing of reaction products to recover the catalyst and the desired components with resulting economic advantages. Certain Group VIII metals such as rhodium or cobalt are utilized in these catalysts. The high cost of these transition metal catalysts makes any increased efficiency in reaction rate or length of life of the catalyst very important.

Typically combined hydroformylation/reduction reactions are carried out by contacting a feed olefin with a gaseous mixture of CO and $H_2$ at a temperature of at least 80° C. and a pressure of at least 1000 psig in the presence of a catalytic amount of transition metal complex catalyst supported by a polymer or resin. This invention involves the unexpected recognition that halogens, specifically chlorine, poison or inhibit the hydroformylation/reduction of olefins to alcohols. Halogens of any source in the reaction will reduce either or both the reaction rate and catalyst life.

One source of halogens are metal halides used in preparation of the catalyst such as in U.S. Pat. No. 4,098,727 directed to $RhCl_3XH_2O$ used to produce a rhodium catalyst supported on a tertiary amine resin. Also, impurities in the solvent, both organic and inorganic, the resin (e.g., a tertiary amine resin in the HCl salt form), quaternary amines present in tertiary amine resins containing chloride counter anions, and halide impurities in the feed olefin are typical halide sources.

The initial reaction rate of a hydroformylation/reduction is adversely limited by a catalyst prepared by the addition of metal halides, and by a tertiary amine resin in the HCl form or with quaternary impurities on the resin in halide form. Deactivation of the hydroformylation/reduction catalyst is observed when halide impurities are present in the feed.

A tertiary amine resin can be washed in a base (e.g., 1.0N NaOH) to change the HCl salt form or quaternary impurities in the chloride form to halide-free forms. Such processes are common in ion-exchange resin technology. The excess base is then removed and the resin dried. In this way halide concentrations are minimized.

The olefin feed and solvent halide concentrations can be controlled and maintained below certain specified limits in order to prevent poisoning of the catalyst. Ideally for hydroformylation/reduction reactions, the concentration is kept less than 100 ppm halide. The catalyst can be prepared without the use of metal halides. Any halide ion within the catalyst can be removed before it is charged to the oxo process reactor. Thus the life of the catalyst and the initial reaction rate of the hydroformylation/reduction reaction are increased by maintaining a substantially halogen-free process. Preferably the halide concentration throughout the process should be reduced to below 100 ppm. Data has shown that 6000 ppm has a significant deactivating effect and even 600 ppm has deactivating results.

In normal usage, a hydroformylation/reduction reaction of olefins to alcohols is accomplished by contacting the olefin feed with a gaseous mixture of CO and $H_2$ at a temperature of at least 80° C. and a pressure of at least 1000 psig in the presence of a catalytic amount of a transition metal complex on an amine functionalized support. The following examples will be illustrative of certain specific embodiments of the invention.

EXAMPLE 1

A rhodium metal complex catalyst supported on a tertiary amine resin such as DOWEX ® MWA-1 resin manufactured by The Dow Chemical Company, toluene, and tetrahydrofuran were placed in a 300 cc autoclave. Operating conditions of 130° C. and 4000 psig were established, and then 90% by weight dicyclopentadiene (DCPD) in solution with toluene was pumped into the reactor. The reaction was monitored by gas chromatography using a UCW-982 column. The data on samples obtained after two hours is presented in Table 1. This data teaches the diminishing impact halides can have on the initial reaction rate. All runs in Table 1 were made with 4 gm resin, 16.8 gm tetrahydrofuran, 74.4 gm toluene with 26.8 ml of 90% DCPD in toluene pumped into the reactor at operating conditions. All data is taken after two hours at 130° C. and 4000 psig.

TABLE I

| Catalyst | Comment | % Selectivity |
|---|---|---|
| $Rh_4(CO)_{12}$ | Amine in HCl form | 6.1 |
| $Rh_4(CO)_{12}$ | NaOH wash resin | 72.9 |
| $Rh_4(CO)_{12}$ | 6.5% Quat Cl | 50.4 |
| $Rh_4(CO)_{12}$ | 9.0% Quat Cl | 37.9 |
| $Rh_4(CO)_{12}$ | 13.1% Quat Cl | 25.4 |
| $Rh_4(CO)_{12}$ | NaOH wash, 0.65 gm NaCl | 76.4 |
| $Rh_4(CO)_{12}$ | NaOH wash, 0.5 cc $MeCl_2$ | 50.7 |
| $RhCl_3 \cdot XH_2O$ | * | 3.3 |

*Prepared with $RhCl_3 \cdot XH_2O$ U.S. Pat. No. 4,098,727, Ex. 7

EXAMPLE 2

An analysis of catalyst resins that had been on stream for different periods of time and corresponding dicyclopentadienedimethanol (DCPD DM) selectivity is given in Table 2. This data shows that halides have a deactivating effect on the catalyst life. The data implies that there is a concentration of halide that is tolerable, though not desirable; as the tolerated concentration is surpassed, the deactivation of the catalyst accelerates.

TABLE 2

| Resin | Reactor | ppm Cl | Selectivity % DCPD DM 2 hr residence | Selectivity % DCPD DM 6 hr residence |
|---|---|---|---|---|
| New Resin | | 620 | 87.5 | 87 |
| Used 125 hrs | Batch | 2800 | 86.8 | — |
| Used 300 hrs | CSTR | 6200 | — | 22 |

The following Table 3 tabulates the percent DCPD DM selectivity versus time for (1) a feed containing chlorine and (2) a chlorine-free feed. The feed containing chlorine produces a lowered percent DCPD DM selectivity over time as compared with the chlorine-free feed. It is demonstrated that chlorine in the feed can reduce catalyst life.

TABLE 3

| Hours of Catalyst Use | % DCPD DM Selectivity | |
|---|---|---|
| | Feed With Chlorine | Feed Without Chlorine |
| 50 | 80+ | 80+ |
| 100 | 80 | 80+ |
| 150 | 75 | 80+ |
| 200 | 65 | 80+ |
| 220 | 64 | 80+ |
| 230 | 60 | 80+ |
| 240 | 57 | 80+ |
| 250 | 53 | 80+ |
| 260 | 47 | 80+ |
| 270 | 40 | 80+ |
| 280 | 35 | 80+ |
| 290 | 30 | 80+ |

While the foregoing is directed to the preferred embodiments of the present invention, other and further embodiments of the invention may be devised without departing from the basic scope thereof, and the scope thereof is determined by the claims which follow.

What is claimed is:

1. A method of enhancing performance of a combined hydroformylation/reduction reaction of an olefin liquid feed in the presence of a resin-supported transition metal complex catalyst, the method comprising the steps of:
   (a) preparing a resin-supported transition metal complex catalyst for use in a combined hydroformylation/reduction reaction substantially free of halides and halide salts in said metal complex catalyst; and
   (b) introducing an olefin liquid feed to the resin-supported catalyst for conducting a combined hydroformylation/reduction reaction, in the presence of CO and $H_2$, wherein the olefin feed has a specified maximum limit of halide concentration sufficiently low to enable continued indefinite operation of the combined hydroformylation/reduction reaction process without halide poisoning.

2. The method of claim 1 further including the step of addition of a solvent to the feed.

3. The method of claim 2 wherein the solvent is maintained at specified limits of halide concentration.

4. The method of claim 3 wherein the halide concentration of the feed and solvent is maintained below 100 ppm.

5. The method of claim 1 wherein the enhanced performance is a higher initial rate of reaction and a longer catalyst life.

6. The method of claim 1 wherein the halide is chlorine.

7. The method of claim 1 wherein the metal complex catalyst contains rhodium.

8. The method of claim 1 wherein the olefin liquid feed is dicyclopentadiene.

9. The method of claim 1 wherein the catalyst support resin is a tertiary amine.

10. The method of claim 1 wherein the reaction is carried out at a temperature of at least 80° C. and a pressure of at least 1000 psig.

11. The method of claim 1 wherein the temperature is 130° C. and the pressure is 4000 psig.

12. The method of claim 1 including the preliminary step of removing substantially all halide ions from the catalyst by washing in a strong base.

13. The method of claim 1 wherein metal halides are eliminated from the preparation of the catalyst.

14. The method of claim 9 wherein tertiary amine in HCl form is converted to a halide free form by washing with a strong base.

15. The method of claim 9 wherein quaternary impurities on the tertiary amine resin in the halide form are converted to a halide-free form by washing with a strong base.

16. The method of claim 1 wherein the halide concentration of the feed is maintained below 100 ppm.

* * * * *